(12) United States Patent
Sela et al.

(10) Patent No.: US 12,066,481 B2
(45) Date of Patent: Aug. 20, 2024

(54) SYSTEM AND METHOD FOR MONITORING ACTIVITY OVER TIME-DOMAIN OF ELECTRICAL DEVICES

(71) Applicant: Isra-Juk Electronics Ltd., Petach-Tikva (IL)

(72) Inventors: Isaac Sela, Petach Tikva (IL); Tomer Sela, Petach Tikva (IL)

(73) Assignee: Isra-Juk Electronics Ltd., Petach-Tikva (IL)

( * ) Notice: Subject to any disclaimer, the term of this patent is extended or adjusted under 35 U.S.C. 154(b) by 85 days.

(21) Appl. No.: 16/956,100

(22) PCT Filed: Dec. 18, 2018

(86) PCT No.: PCT/IL2018/051371
§ 371 (c)(1),
(2) Date: Jun. 19, 2020

(87) PCT Pub. No.: WO2019/123457
PCT Pub. Date: Jun. 27, 2019

(65) Prior Publication Data
US 2021/0102993 A1 Apr. 8, 2021

Related U.S. Application Data

(60) Provisional application No. 62/607,341, filed on Dec. 19, 2017.

(51) Int. Cl.
*G01R 31/28* (2006.01)
*G01R 31/52* (2020.01)
*G16H 40/67* (2018.01)

(52) U.S. Cl.
CPC ......... *G01R 31/2832* (2013.01); *G01R 31/52* (2020.01); *G16H 40/67* (2018.01)

(58) Field of Classification Search
CPC ... G01R 31/52; G01R 31/2832; H02H 1/0015
See application file for complete search history.

(56) References Cited

U.S. PATENT DOCUMENTS 5,757,596 A * 5/1998 Weber .................. H02H 7/0833
361/115
7,337,353 B2 * 2/2008 Yamamoto .......... G06F 11/0727
714/E11.089

(Continued)

FOREIGN PATENT DOCUMENTS

EP 2187276 B1 5/2010
JP 2005202554 7/2005

OTHER PUBLICATIONS

International Search Report for PCT application No. PCT/IL2018/051371, mailed on Apr. 23, 2019.

*Primary Examiner* — Chirag R Patel
(74) *Attorney, Agent, or Firm* — PEARL COHEN ZEDEK LATZER BARATZ LLP

(57) ABSTRACT

System and method, in the field of device control, for detecting and processing one or more deviations from an acceptable electrical behavior in an electrical device are provided here. The system may include a sampling unit for receiving at least one activity indication, a storage to store acceptable values related to the acceptable electrical behavior, an active time measurement unit to receive the activity indication and measure an active time duration, an inactive time measurement unit to receive the activity indication and measure an inactive time duration and a deviation processor to compute values derived from the activity indication, the active time duration and the inactive time duration, detect and analyze one or more deviations between the acceptable values and the derived values.

17 Claims, 8 Drawing Sheets

(56) References Cited

U.S. PATENT DOCUMENTS

| | | | |
|---|---|---|---|
| 9,632,828 B1* | 4/2017 | Mehta | H04L 12/00 |
| 10,581,874 B1* | 3/2020 | Khalid | G06F 21/562 |
| 2001/0039190 A1* | 11/2001 | Bhatnagar | D06F 34/28 |
| | | | 455/450 |
| 2008/0270071 A1 | 10/2008 | Marvasti et al. | |
| 2012/0303674 A1* | 11/2012 | Boensch | G06F 16/252 |
| | | | 707/802 |
| 2013/0033978 A1* | 2/2013 | Eckert | H04L 45/28 |
| | | | 370/216 |
| 2014/0211906 A1* | 7/2014 | Herbeck | H03K 23/40 |
| | | | 377/47 |
| 2016/0131694 A1* | 5/2016 | Chen | H05B 47/22 |
| | | | 324/539 |
| 2018/0096157 A1* | 4/2018 | Israel | H04L 63/1416 |
| 2018/0143081 A1* | 5/2018 | Van Endert | G05B 15/02 |
| 2019/0124744 A1* | 4/2019 | Pandharipande | H05B 45/10 |

\* cited by examiner

SYSTEM AND METHOD FOR MONITORING ACTIVITY OVER TIME-DOMAIN OF ELECTRICAL DEVICES

CROSS-REFERENCE TO RELATED APPLICATIONS

This application is a National Phase Application of PCT International Application No. PCT/IL2018/051371, International Filing Date Dec. 18, 2018, entitled "SYSTEM AND METHOD FOR MONITORING ACTIVITY OVER TIME-DOMAIN OF ELECTRICAL DEVICES", published on Jun. 27, 2019 as International Patent Application Publication No. WO 2019/123457, claiming the benefit of U.S. Provisional Patent Application No. 62/607,341, filed Dec. 19, 2017, which is incorporated herein by reference in its entirety.

BACKGROUND OF THE INVENTION

Prior to setting forth the background of the invention, it may be helpful to set forth definitions of certain terms that will be used hereinafter:

The term "rules" as used herein is defined as limitations and requirements set by a person.

The term 'duty-cycle' as used herein is defined as the percentage of the activity time as part of the activity cycle of the apparatus being monitored.

The term 'session duration' as used herein is defined as the duration of a series of activities of an electrical or electro-mechanical device that occur in sequence and are related one to the other. For example, a washing machine performs several activities like filling water, heating water, turning the drum and draining—after being set to work by a person. These activities occur one after the other. A complete sequence of machine wash is composed of several such activities. Such a sequence of activities is referred in this application as an "activity session". The duration of the "activity session" is referred as "session duration".

The present invention relates to the field of device control. More particularly, the invention relates to controlling the operation of devices over time-domain, using time-domain rules that can be updated during the operation of the devices.

Many faults in operation of devices are detected by controlling physical measures as voltage, current, temperature, humidity, speed, height, pressure etc. The results of the measurements are compared to a set of one or more acceptable values. An un-acceptable value resulted from such a measurement is, in many cases, an indication of a fault. It is known in electrical systems to use protection devices that protect against faults characterized by electrical parameters such as voltage and current. It is known in mechanical devices to use protection devices that protect against faults characterized by mechanical parameters such as temperature, speed, torque and pressure.

However, there is one measure that is not currently covered in faults detection—the measurement of time. In practice—the operation over time-domain of many devices can be analyzed to detect many faults. In many cases—the change in the operation over time domain can be detected before other fault-indications can be detected.

Time-domain characteristics of many devices vary over days, weeks or months. The duty-cycle of a compressor of a refrigerator in a dwelling unit is expected to be low between 2 a.m. and 5 a.m.—as it is the middle of the night. But for the same refrigerator—it can be expected that the compressor's duty-cycle may be higher during the lunch time of 1 p.m. to 3 p.m. The duty-cycle may also vary along the year—at the middle of the winter the compressor of a refrigerator is expected to be more idling than in a hot summer day.

SUMMARY OF THE INVENTION

According to embodiments of the present invention, there is provided a system and a method for detecting and processing one or more deviations from an acceptable electrical behavior in an electrical or electro-mechanical device. The system may include a sampling unit for receiving at least one activity indication, a storage to store acceptable values related to the acceptable electrical behavior, an active time measurement unit to receive the activity indication and measure an active time duration, an inactive time measurement unit to receive the activity indication and measure an inactive time duration and a deviation processor to compute values derived from the activity indication, the active time duration and the inactive time duration, detect and analyze one or more deviations between the acceptable values and the derived values.

Furthermore, according to embodiments of the present invention, the system may further include an activity filter.

Furthermore, according to embodiments of the present invention, the activity indication may a digital signal or an analog signal.

Furthermore, according to embodiments of the present invention, the derived values may be a duty cycle, a session duration.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
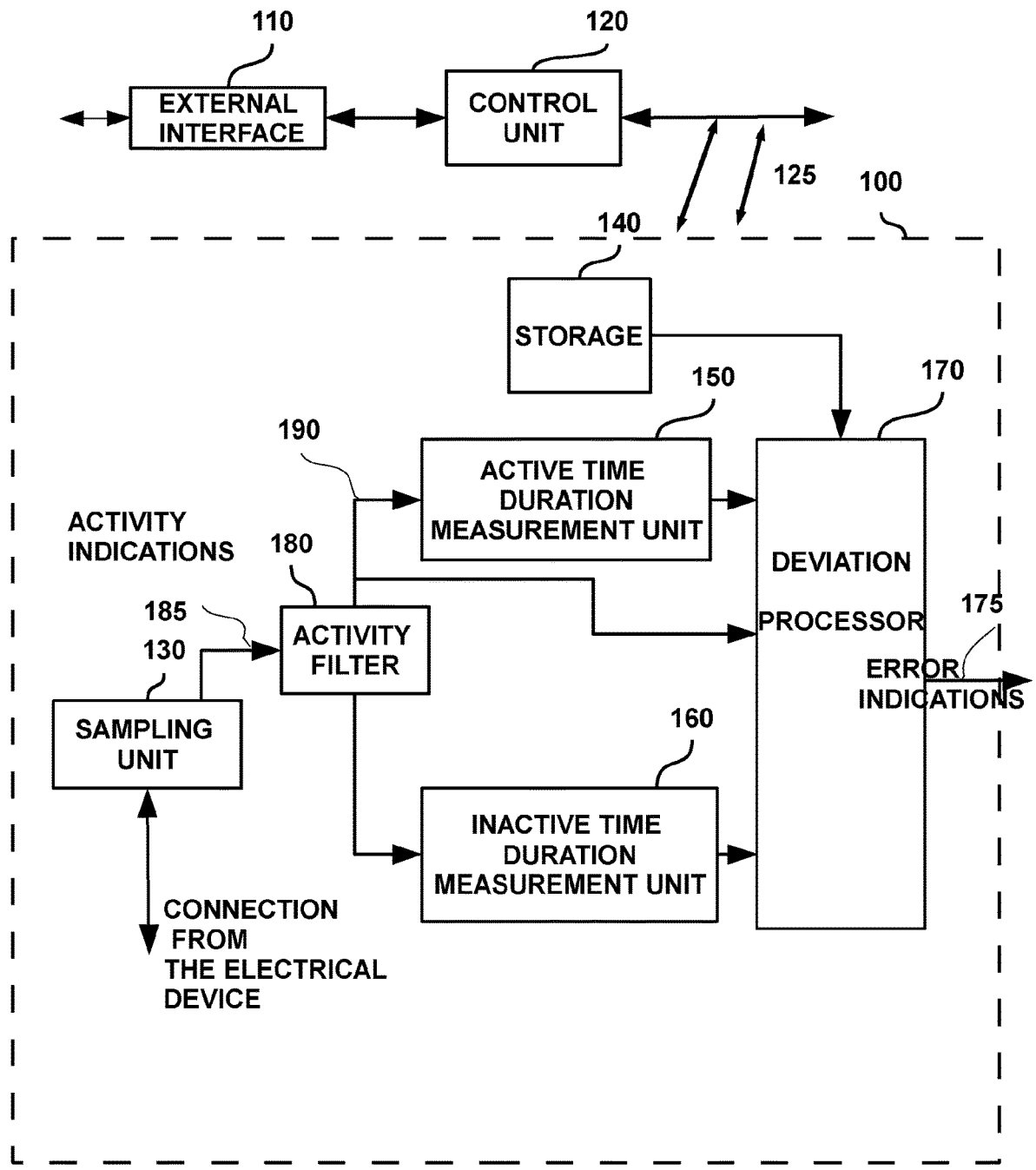
FIG. 1 is a high-level block diagram of the proposed system according to some embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

Some aspects of the present invention may be related to a method and a system for automatically and continuously monitoring and detecting electrical or electro-mechanical faults in an electrical or electro-mechanical device. Operation over time-domain of many devices may be analyzed to detect many faults. By setting rules for operation over the time-domain and checking device-behavior against those rules—problems and malfunctions can be detected. In many cases—this check can detect device-operation faults before they affect other device-operation parameters.

Embodiments of the invention may be directed to automatically and continuously monitoring and detecting electrical faults by detecting deviation from an acceptable electrical behavior of the device. As used herein, electrical behavior may be defined by one or more values of one or more parameters associated with time-domain characteristics of the device—that are indicative of the behavior of the device. For example, leakage of gas in a cooling system like a refrigerator may lead to longer operation of the compressor, hence a higher duty-cycle of operation over time-domain. The gas-leakage may initially not affect the temperature of the cooled system; hence a temperature-sensor may not detect a fault. However, time-domain analysis of the operation of the compressor may show a change from the proper operating-condition—the duty-cycle of the compressor may increase. In such a case, the operation over time-domain analysis may enable earlier detection of the formation of the fault in the cooling system—decreasing amount of gas. In such a manner, the fault may be detected before the cooling-capability itself is affected. As an additional example: a fault in a thermostat of an electrical oven—being stuck at the "closed-circuit" state. The malfunctioning thermostat may not disconnect the heating-element when the oven reaches a pre-defined temperature-level. This may lead to excessive heating of the oven and can even ignite fire. A properly-functioning thermostat should open the electrical-circuit after working for a reasonable time. However, time-domain analysis of the operation of the thermostat may detect that the thermostat is continually closing the electrical circuit. Thus, the fault in the thermostat may be detected—before fire ignites.

There is a need to set time-domain rules for controlling the operation of devices and to be able to modify the rules on-the-fly—during the operation of the device, without disrupting the operation of the device. The ability to modify the time-domain rules—has more additional advantages:

The same control unit can be used for various products and devices

The rules can be adopted during a learning-phase

The rules can be set from a remote-control unit

The rules can even be loaded from external sources like the internet

The rules can be obtained from the manufacturer of the electrical or electro-mechanical device Rules can be obtained from a man/machine interface Rules can be obtained from a given file of rules A list of various exemplary electrical devices and the monitoring that may be relevant to them is given in table 1 hereinunder:

TABLE 1

| APPLIANCE | MIN/MAX "ON" TIME | MIN/MAX "OFF" TIME | MIN/MAX DUTY-CYCLE | MIN/MAX SESSION DURATION | Possible fault(s) |
|---|---|---|---|---|---|
| Toaster | MIN/MAX "ON" | | | | Timer stuck at active state or timer stops too fast |
| Vacuum-Cleaner | MAX "ON" | | | | Vacuum-Cleaner left to work too much time - maybe forgotten. |
| Radiator | MAX "ON" | MIN "OFF" | | | Faulty thermostat |
| Air-Conditioner | | | MIN/MAX | | Faulty thermostat or gas leakage |
| Washing Machine | | | | MIN/MAX | Faulty thermostat, water-supply problem, faulty timer |
| Clothes-Dryer | | | | MIN/MAX | Faulty timer |
| Refrigerator | MAX "ON" | MAX "OFF" | MIN/MAX | | Faulty thermostat or gas leakage |
| Oven | MIN/MAX | | | MIN/MAX | Faulty thermostat |
| Dish-Washer | | | | MIN/MAX | Faulty thermostat, water-supply problem, faulty timer |

TABLE 1-continued

| APPLIANCE | MIN/MAX "ON" TIME | MIN/MAX "OFF" TIME | MIN/MAX DUTY-CYCLE | MIN/MAX SESSION DURATION | Possible fault(s) |
|---|---|---|---|---|---|
| Industrial Compressor | MAX "ON" | MIN "OFF" | MIN/MAX | | gas leakage, faulty pressure sensor |
| Industrial water-pump | MAX "ON" | | MIN/MAX | | water-supply problem, faulty pressure sensor |

Reference is now made to FIG. 1 which presents a high-level block diagram of the proposed system according to some embodiments of the invention.

The system 100 may include a sampling unit 130, an active time duration measurement unit 150, an inactive time measurement unit 160, at least one storage unit 140, and a deviation processor 170. In some embodiments, system 100 may further communicate with a control unit 120 and an external interface 110. In some other embodiments, system 100 may include an activity filter 180.

The system 100 may receive rules of operation such as minimum/maximum values of operation over time domain from local or remote source, e.g. control unit 120 and store them at the at least one storage 140. These values may be specified in the same units in which the system 100 counts time.

These can be, for example, seconds or clock cycles of an oscillator. A local source or a remote source e.g. the control unit 120 may specify more than one minimum/maximum set of values for each of the checks being performed. This can be used when any of the measurements has several ranges of acceptable values.

The output of sampling unit 130 may be activity indications 185—which reflect the indications received from an electrical or electro-mechanical device (not shown) that is being monitored. In some embodiments, the activity indications 185 may be received from a sensor device (not shown) connected to the electrical or electro-mechanical device. Activity-indication 185 may be an analog signal or a digital signal. According to some embodiments of the present invention, the activity-indications 185 may be filtered by the activity-filter 180. This filtering may be required to reduce noise on noisy activity-indications. The activity-filter 180 may also be used to convert an analog input on activity-indication 185 into a digital signal. In alternating current (AC) systems—the electrical current drawn by a load varies significantly along each AC cycle. In such a case, the activity filter may determine the activity status of the electrical or electro-mechanical device being monitored—for each AC cycle. The activity filter 180 may determine this by sampling the electrical-current in plurality of points on each AC cycle, make computations based on the values sampled and compare the result of the computation to an externally defined threshold. Root-Mean-Square (RMS) is a common computation method for electrical current. Signal 190 may be the output of activity-filter 180 or it may be a replica of activity-indications signal 185 itself.

Signal 190 may be a digital signal with two discrete values. One value of signal 190 indicates that the device being monitored is active and the other value indicates that the device being monitored is inactive. Signal 190 may enter to the active time duration measurement unit 150 and to the inactive time duration measurement unit 160 which measures the "active" and "inactive" durations of signal 190.

When the device being monitored is active—the duration of the "active" period is measured in active time measurement unit 150. When the device being monitored is inactive—the duration of the "inactive" period is measured in inactive time measurement unit 160. Units 150 and 160 may update their outputs upon the end the periods they measure. Thus, measurement unit 150 may update its "active" duration output when the device being monitored becomes inactive. Measurement unit 160 may update its "inactive" duration output when the device being monitored becomes active. Measurement units 150 and 160 may also indicate counting-overflow when such counting-overflow occurs. Measurement units 150 and 160 may also indicate counting-underflow. Counting-underflow indication from a counter may indicate that counting has not yet started by the counter after power-up of system 100 or after the counter have been reset.

The outputs of the measurement units 150 and 160 may then enters to a deviation processor 170. Deviation processor unit 170 may then compute one or more values derived from signal 190, the active time duration and inactive time duration. In some embodiments, the deviation processor 170 may compute the duty-cycle of the activity periods of the electrical or electro-mechanical device being monitored. Deviation processor 170 may indicate that the duty-cycle is not valid. In cases when counting-overflow or counting-underflow is received by the deviation processor 170 from measurement units 150 or unit 160—the duty-cycle computation is invalid. This may be indicated by the deviation processor 170. In some other embodiments, deviation processor 170 may compute session duration variable. Session start may be indicated by a value of "active" on signal 190. Session end may be determined by deviation processor 170 after signal 190 indicates the value of "inactive" for a predefined duration. Deviation-processor 170 may further receive one or more acceptable values related to the electrical behavior. The acceptable values may be related to any time domain value, such as session duration, duty cycle, and active/inactive time duration. The one or more acceptable values may be received from storage 140. Additionally, or alternatively the acceptable values related to the electrical behavior may be received from a storage unit associated with an external source, for example, associated with control unit 120, for example, via external interface 110 (e.g., over the internet). Deviation processor 170 may analyze the one or more deviations between the one or more acceptable values and the one or more derived values. Deviation processor 170 may check the output of the measurement unit 150 against minimum and maximum values. Similarly, deviation processor 170 may check the output of measurement unit 160, the duty-cycle computed value, and the session duration computed value. Deviation processor 170 may generate error indication signals (not shown) in case the values received from units 150, 160 and any derived values respectively—are out of the acceptable values and may combine the error indication signals into one error indication signal or alert 175. Deviation processor may perform additional processing on the error indication signals.

Such processing may include filtering of too-short indications, for example. Such processing may additionally include logic that takes the counting-overflow, counting-underflow and validity indications into account. The error indication signal 175 is an output of system 100. Deviation-processor 170 may further be configured to send an alert 175 via external interface to a user or an external device (not shown).

Deviation-processor 170 may be any computation platform that may be configured to detect one or more deviations from an acceptable electrical behavior, the electrical behavior being related to a time-domain waveform. Deviation-processor 170 may include a processor, for example, a central processing unit processor (CPU), a digital device or part of it, a chip or any suitable computing or computational or digital-logic device. Deviation-processor 170 may further include a memory 140 for storing code or instructions to be executed by deviation-processor 16, for example instructions related to a method of detecting one or more deviations from an acceptable electrical behavior. The memory may be any non-volatile readable medium and/or non-volatile storage medium, such as for example an electrical memory, a disk drive, or a USB flash memory for storing instructions, e.g., computer-executable instructions, which, when executed by the deviation-processor 170, carry out methods disclosed herein.

In some embodiments, the values measured or computed by measurements units 150, 160 and the deviation processor 170 may be transmitted to external interface 110. Additionally, measurements units 150, 160 and the deviation processor 170 may transmit the counting-overflow, counting-underflow and validity indications from these blocks. Thus, these values can be analyzed, monitored and used for purposes like statistics, monitoring improvement or any other purpose.

In some embodiments, measurement units 150, 160 and deviation processor 170 are included in a single computer platform.

System 100 may be implemented in a hardware implementation by an FPGA, an ASIC, discrete logic components, a processor or combinations of them. In such an embodiment the hardware may be fed by an analog-to-digital converter that samples the electrical current consumed by the device being monitored. System 100 may also be implemented by a software code using a CPU and an analog-to-digital converter. Another way that may be used to implement system 100 is by software code that is executed using a digital signal processor (DSP) that has a built-in analog-to-digital converter.

Figure 2:
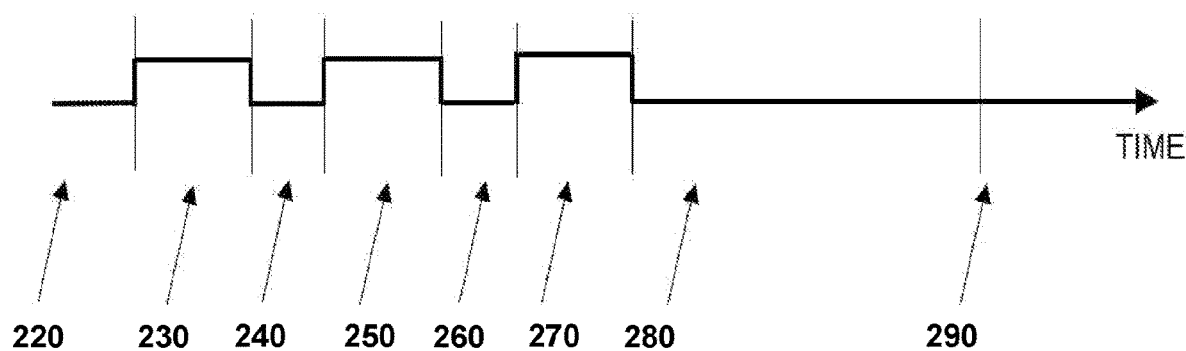
FIG. 2 depicts time-domain waveform used to explain the measurements of the "active" and "inactive" durations and the duty-cycle computation.

Reference is now made to FIG. 2. FIG. 2 may be used to explain the way "active-duration", "inactive-duration" and "duty-cycle" of the activity-indication 185 are computed. FIG. 2 depicts waveforms that may be found on the signal 190 that is the input of the blocks that make measurements and computations—derived from the states of the monitored electrical or electro-mechanical device. Sections 230, 250 and 270 of the waveform describe "active" periods. Sections 220, 240, 260 and 280 of the waveform describe "inactive" periods.

To measure duration of the "active" time—active time measurement unit 150 may find the presence of an "inactive" indication 220 on signal 190. After the "inactive" indication 220 is found, active time measurement unit 150 waits for the "active" indication 230. When the "active" indication 230 is found—active time measurement unit 150 may count the duration of the "active" time. This counting is continued until the "active" state ends or the "active" duration counter reaches an overflow state. In case that the "active" state ended with a counter overflow—active time measurement unit 150 may set the overflow indication at its output. In case that the measurement ended without a counter-overflow—active time measurement unit 150 may set the measured "active" duration at its output and may indicate that its output is valid.

To measure duration of the "inactive" time—inactive time measurement unit 160 may find the presence of an "active" indication 230 on signal 190. This is done in order to avoid starting the measurement of the "inactive" period while signal 190 is already in the "inactive" state. At this step—inactive time measurement unit 160 may indicate that its outputs are "invalid". After the "active" indication 230 is found, inactive time measurement unit 160 may wait for the "inactive" indication 240. When the "active" indication 240 is found—inactive time measurement unit 160 may count the duration of the "inactive" time. This counting is continued until the "inactive" state ends or the "inactive" duration counter reaches an overflow state. In case that the "inactive" state ends with a counter overflow—inactive time measurement unit 160 may set an overflow indication at its output.

In case that the measurement ended without a counter-overflow—"active" state 250 started—inactive time measurement unit 160 may set the measured "inactive" duration at its output and may indicate that its output is valid.

At the beginning of section 250 of the waveform of FIG. 2—the duty-cycle of the activity at sections 230 and 240 may be computed by deviation processor 170. In a repetitive signal—the duty-cycle may be computed for every "active" and its successive "inactive" periods. However, there may be cases in which the duty-cycle of a signal cannot be computed. Sections 270 & 280 of FIG. 2 depict such a case. After the "active" period 270 there is an "inactive" period 280 that does not end. In such a case—deviation processor 170 may determine that period 280 is endless when the time that elapsed from the end of the "active" period 270 reaches a limit as defined by 290. Deviation processor 170 may, in such a case, generate and indication that it cannot compute duty-cycle for the signal 190.

Figure 3:
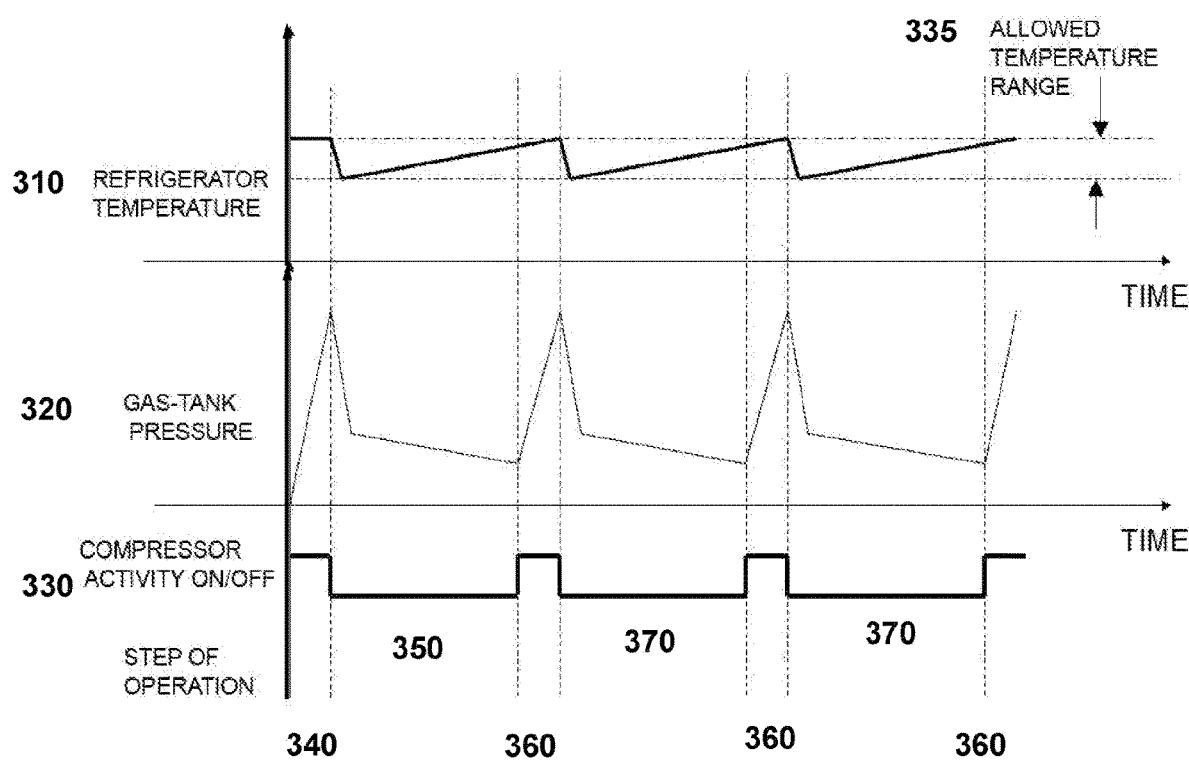
FIG. 3 is a schematic representation of an exemplary graphical description of an operation of a compressor of a refrigerator that functions properly.

Reference is now made to FIG. 3, which is a schematic representation of an exemplary graphical description of an operation of a compressor of a refrigerator that functions properly. FIG. 3 may describe normal operation of a compressor of a refrigerator. Upon power-up (steps 340 and 350)—the compressor may work and the pressure 320 in the gas-tank of the refrigerator may increase. As the pressure reaches a predefined pressure level—the compressor may stop its operation. The gas-tank valve is opened, and the temperature in the refrigerator may decrease—step 350. As the time passes—the temperature may increase. When the temperature increases to its highest allowed level 335—the compressor may work again (step 360). The pressure in the gas-tank may increase until it reaches a predefined level. The temperature in the refrigerator may continue to rise—until the gas-tank valve is opened again—step 370. The activity of the compressor in this manner is described by waveform 330. This behavior continues repeatedly.

Figure 4:
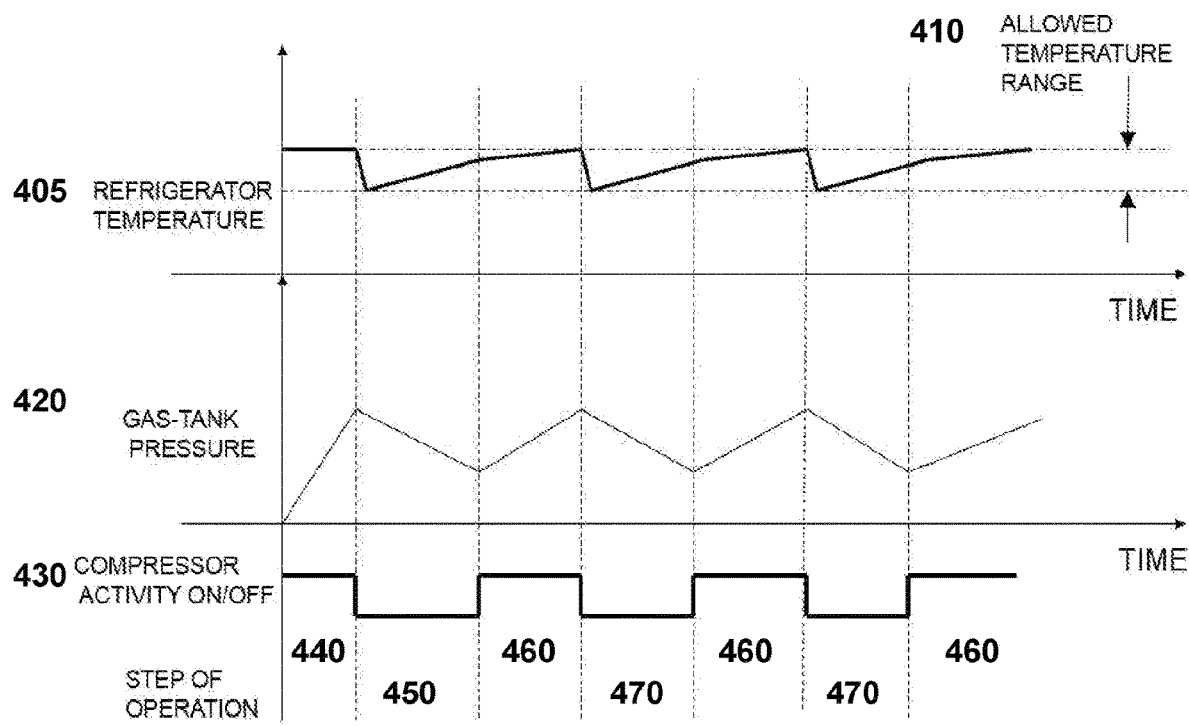
FIG. 4 is a schematic representation of an exemplary graphical description of an operation of a compressor of a refrigerator that functions improperly.

FIG. 4 is a schematic representation of an exemplary graphical description of an operation of a compressor of a refrigerator that functions improperly. It describes the operation of the refrigerator's compressor when a significant part of the gas has evaporated, according to some embodiments of the present invention. The initial pressurizing phase 440 on FIG. 4—the bad condition—is longer than the initial phase 340 on FIG. 3—the good condition. The gas-tank pressure 420 in FIG. 4 may not reach the levels 320 seen on FIG. 3—due to lack of gas. As a result, the refrigerator's temperatures 405 in FIG. 4—may rise faster than in the good condition 310 of FIG. 3. The activity of the compressor in this manner may be described by waveform 430. The compressor's duty-cycle computed for 460 and 470 in FIG. 4 is much higher than the duty-cycle computed for 360 and 370 of FIG. 3.

Figure 5:
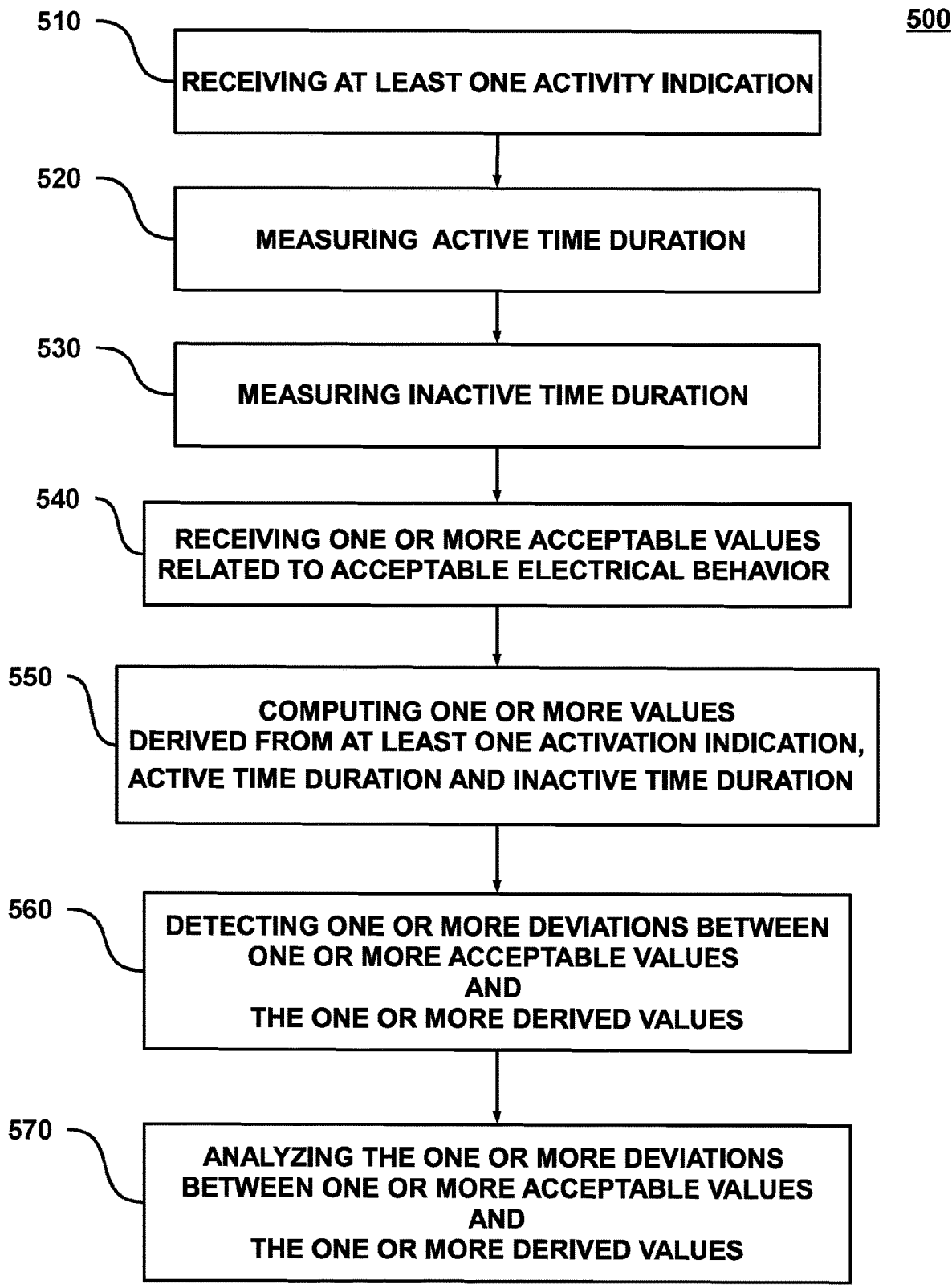
FIG. 5 is a flowchart that depicts a method of detecting and processing one or more deviations from an acceptable electrical behavior in an electrical or electro-mechanical device according to some embodiments of the present invention.

Reference is now made to FIG. 5 that is a flowchart of a detecting and processing one or more deviations from an acceptable electrical behavior in an electrical device according to some embodiments of the present invention. The method of FIG. 5 as well as other methods according to embodiments of the invention may be performed by a system for detecting one or more deviations from an acceptable electrical behavior at a point of interest in an electrical network, for example, system 100.

In operation 510, the method may include receiving at least one activity indication. The method may then include measuring active time duration as per step 520 and measuring inactive time duration as per step 530, as detailed previously. The method may include receiving one or more acceptable values related to the acceptable electrical behavior, as per step 540.

The one or more acceptable values related to the electrical behavior may be received from an external device, for example, a database related to a manufacturer of the electrical or electro-mechanical device (e.g. the website of a washing machine manufacturer). In some embodiments, the one or more values related to the electrical behavior may be learned by the system 100 by being measured over time, analyzed, filtered and/or processed by measurement units 150 and 160 and/or deviation-processor 170 and then stored in storage 140 and used as acceptable values related to the electrical behavior.

In step 550, the method may include computing one or more values derived from at least one activation indication, active time duration and inactive time duration. In some embodiments, the method may include computing session duration derived from signal 190, as described later in FIG. 8. In some other embodiments, the method may include computing the duty-cycle, as described later in FIG. 6, derived from active time duration and inactive time duration.

In step 560, the method may include detecting one or more deviations between one or more acceptable values and the one or more values.

In step 570, the method may include analyzing the one or more deviations between one or more acceptable values and the one or more derived values, as detailed above.

Figure 6:
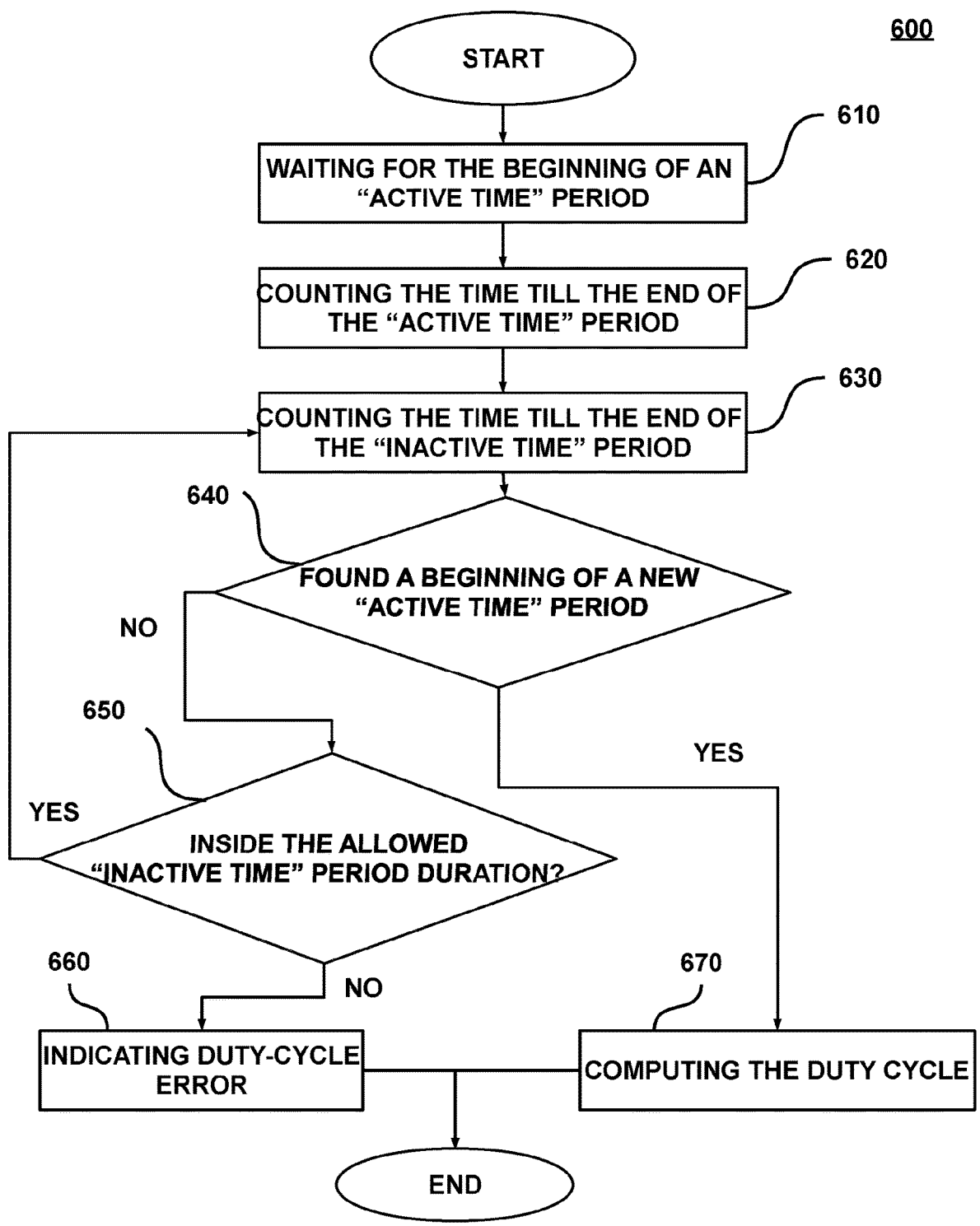
FIG. 6 is a flowchart that depicts the process of computing the duty-cycle of the activity-indication received from the unit being controlled according to some embodiments of the present invention.

Reference is now made to FIG. 6. This figure depicts the process of computing the duty-cycle of the signal 190, according to some embodiments of the present invention. This sequence of operations may be implemented by a state-machine or a processor by deviation processor 170, for example. The duty-cycle computation begins when the signal 190 enters the "active" state 230. In step 610, the state-machine may wait for the beginning of an "active" period. When such an "active" period begins—the state-machine may count the time till the end of the "active" period—at stage 620. When the "active" period ends—the "inactive" period begins. The state-machine may then count the time till the end of the "inactive time" period, as per step 630 (till beginning at a new "active" period. When a new "active" period is found as per step 640—the duty-cycle percentage of the signal 190 may be computed as per step 670. The computation may be done by dividing the duration of "active" period 230 by the sum of the "active" and "inactive" periods 230 and 240. If a new "active" period is not found in step 640—then the state-machine may check for excessive "inactive" duration. In such a case—then at step 650 the deviation processor may indicate that an error occurred during the computation of the duty-cycle of signal 190. Deviation processor 170 may also indicate that its output is invalid in case when measurement units 150 or 160—that feed deviation processor 170—indicate that at least one of their outputs is invalid or has an overflow condition.

Figure 7:
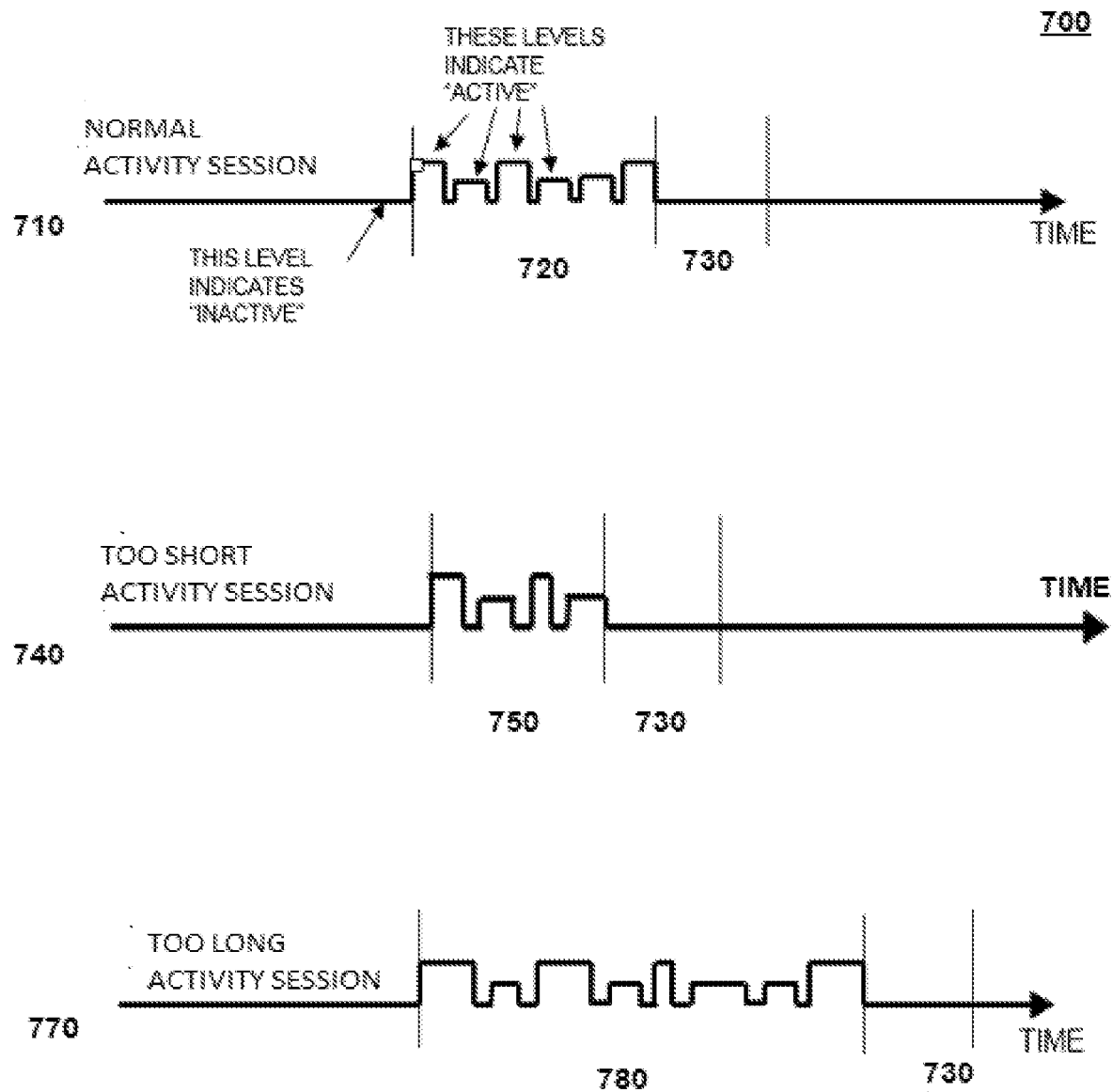
FIG. 7 is a schematic representation of time-domain waveforms used to explain the session-duration measurement.

Reference is now made to FIG. 7. This figure is a schematic representation of time-domain waveforms that might be found on activity indications 185. Such waveforms may be found when the system 100 monitors an electrical or an electro-mechanical device that has activity-sessions. The activity-filter 180 may modify the multiple-level signal 185 shown in FIG. 7 into two levels only on signal 190. By so, the distinction between "active" and "inactive" states by measurement units 150, 160 and deviation processor 170 may be simpler. Waveform 710 describes a normal activity-session of a specific electrical or electro-mechanical device. Part 720 of waveform 710 is the activity-session of the device. Part 730 is an idle time that may be used to determine that the activity-session 720 had ended—just by monitoring the electrical-current drawn by the monitored device. In case that there is a problem in the monitored device that may cause its activity-session to become shorter—the waveform of the electrical-current drawn by the monitored device may show a shorter activity-duration. For example, this is shown by waveform 740, where part 750 of the waveform may indicate the shorter-than-normal activity duration. In such a case—after period 750 elapses—the duration of waveform 750 may be detected as too short and an error may be generated.

Figure 8:
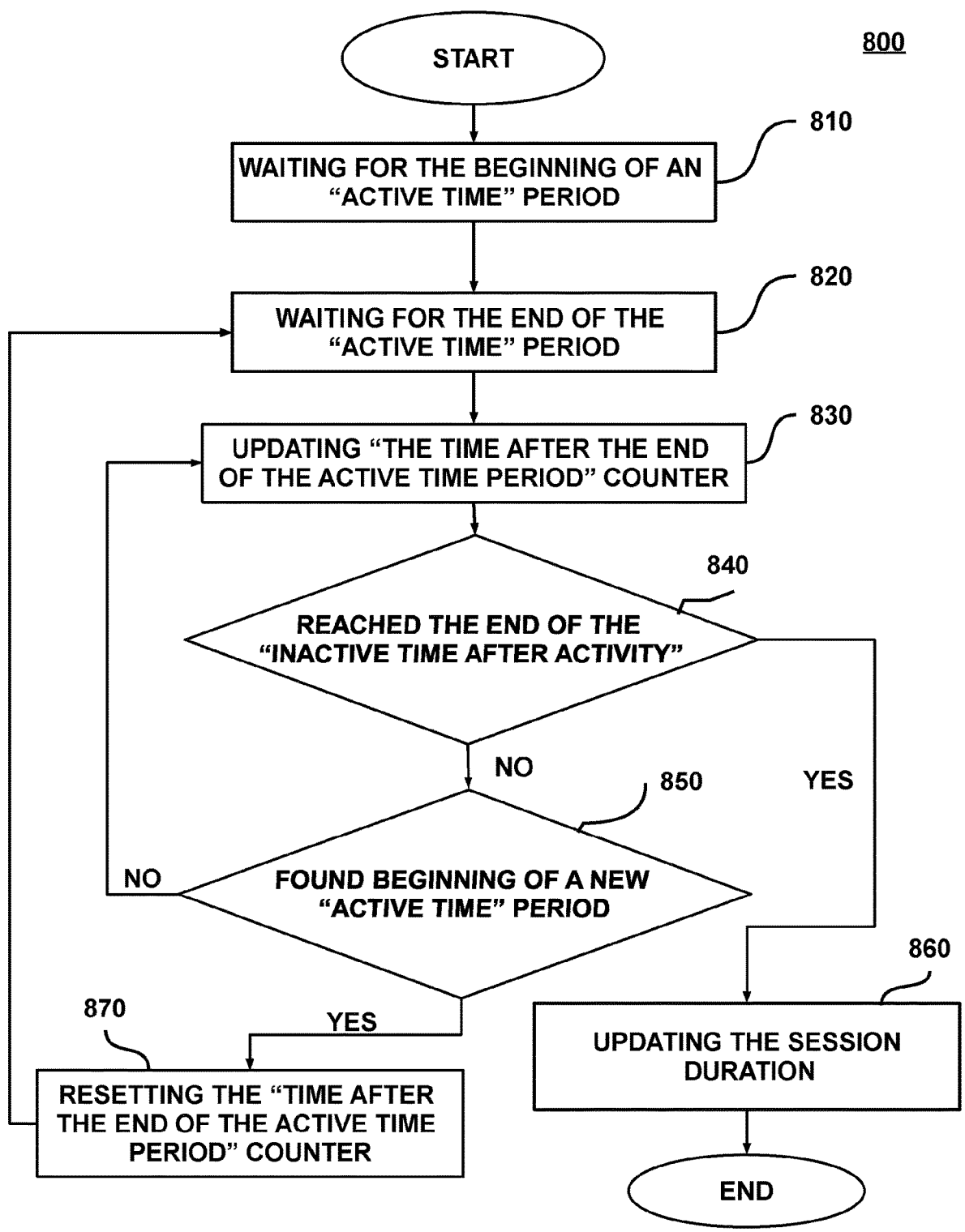
FIG. 8 depicts in a flowchart the process of measuring the session-duration of the activity-indication received from the unit being controlled according to some embodiments of the present invention.

Reference is now made to FIG. 8. FIG. 8 depicts the sequence of operations that may be performed by the system 100 for measuring "session-duration" on the activity indication 185, according to some embodiments of the present invention. The sequence may start when signal 190 is in the "inactive" state. At step 810, the method may include waiting for the beginning of an "active time" period. When such a beginning is found, the method may include counting the session duration and move to step 820. In step 820, the method may wait for the end of the "active time" period while updating the session-duration counter. When the end of the "active" period is found—the method may move to step 830 and update the "time after the end of the active-time period" counter and the session-duration counter. The method may include checking the value of the "time after the end of the active-time period" counter against a limit that may be predefined or may be received by control signal 125, as per step 840. If the result of the check is that the "time after the end of the active-time period" counter reached the limit—then the method may include setting the session-duration value, as per step 860. If the result of the check at step 840 is that the "time after the end of the active-time period" counter did not reach the limit—then then the method may include checking for indication of a new "active" period on signal 190 as per step 850. If signal 190 indicates that a new a new "active" period has started—then the method may include resetting the "time after the end of the active-time period" counter as per step 870 and move to step 820. If signal 190 indicates that a new a new "active" period did not start—then the method may return to step 830—to continue counting the "time after the end of the active-time period". It should be noted that the deviation processor 170 may count the session duration during all the steps performed from the start of the sequence at step 810 till the end of the sequence at step 860.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A system for detecting and processing one or more deviations from an acceptable electrical behavior in an electrical device or in an electro-mechanical device, the system comprising:
    a sampling unit connected to the electrical device or the electro-mechanical device, which samples at least one activity indication of the electrical device or the electro-mechanical device;
    at least one data storage device which stores one or more acceptable values related to the acceptable electrical behavior;
    an active time measurement unit which receives the at least one activity indication and measure an active time duration, which is a time duration in which the electrical device or the electro-mechanical device perform an electrical or an electromechanical activity;
    an inactive time measurement unit which receives the at least one activity indication and measure an inactive time duration which is a time duration in which the electrical device or the electro-mechanical device do not perform an electrical or an electromechanical activity;
    a deviation processor which:
        receives the at least one activity indication, the active time duration, and the inactive time duration;
        detects one or more deviations between time-domain characteristics defined by the at least one activity indication, the active time duration and inactive time duration and time-domain characteristics defined by the one or more acceptable values; and
        carry out time-domain analysis of the one or more said deviations, to determine a type of fault at the electrical device or the electro-mechanical device, based on a type of the electrical device or the electro-mechanical device and the acceptable electrical behavior thereof.

2. The system according to claim 1, wherein the at least one activity indication is a digital signal.

3. The system according to claim 1, wherein the al least one activity indication is an analog signal.

4. The system according to claim 1, wherein the sampling unit is further comprising an activity filter, wherein the activity filter is configured to reduce noise on the at least one activity indication.

5. The system according to claim 4, wherein in case the at least one activity indication is an analog signal and the activity filter is configured to convert the at least one activity indication into a digital signal.

6. The system according to claim 1, further comprising a control unit; and an external interface, wherein the control unit is further configured to receive the one or more acceptable values related to the electrical behavior from an external source.

7. The system according to claim 6, wherein the control unit is further configured to receive the one or more values derived from at least one of the active time duration and inactive time duration and send an alert via the external interface when the analyzed deviation is higher than a threshold value.

8. The system according to claim 7, wherein the alert is sent to at least one of: a user and an external device.

9. The system according to claim 1, wherein the active time measurement unit, the inactive time measurement unit and the deviation processor are included in single processing platform.

10. The system according to claim 1, wherein the electrical behavior is related to maximum and minimum values of at least one of: active time duration, inactive time duration, session duration and duty-cycle.

11. A method for detecting and processing one or more deviations from an acceptable electrical behavior in an electrical device or an electro-mechanical device, the method comprising:
    sampling, via a sampling unit connected to the electrical device or the electro-mechanical device, at least one activity indication of the electrical device or the electro-mechanical device;
    measuring an active time duration, which is a time duration in which the electrical device or the electro-mechanical device perform an electrical or an electromechanical activity;
    measuring an inactive time duration, which is a time duration in which the electrical device or the electro-mechanical device do not perform an electrical or an electromechanical activity;
    storing on a data storage device, one or more acceptable values related to the acceptable electrical behavior;
    computing one or more values derived from the at least one activity indication, the active time duration and inactive time duration;
    detecting one or more deviations between time-domain characteristics defined by the at least one activity indication, the active time duration and inactive time duration and time-domain characteristics defined by the one or more acceptable values; and
    carrying out time-domain analysis of the one or more said deviations, to determine a type of fault at the electrical device or the electro-mechanical device, based on a type of the electrical device or the electro-mechanical device and the acceptable electrical behavior thereof.

12. The method according to claim 11, wherein the at least one activity indication is a digital signal.

13. The method according to claim 11, wherein the at least one activity indication is an analog signal.

14. The method according to claim 11, further comprising sending an alert when the analyzed one or more deviations is higher than a threshold value.

15. The method according to claim 11, wherein receiving one or more acceptable values related to the acceptable electrical behavior is from an external source.

16. The method according to claim 11, wherein the electrical behavior is related to maximum and minimum values of at least one of: active time duration, inactive time duration, session duration and duty-cycle.

17. The method according to claim 11, wherein receiving the one or more acceptable values related to the electrical behavior is from a storage comprising previously detected and analyzed at least one of: active time duration, inactive time duration, session duration and duty-cycle.

\* \* \* \* \*